United States Patent [19]

Sato et al.

[11] Patent Number: 4,465,662
[45] Date of Patent: Aug. 14, 1984

[54] ORAL COMPOSITIONS OF TRANEXAMIC ACID AND CARVONE

[75] Inventors: Hiroshi Sato, Tokyo; Haruo Watanabe, Higashikurume; Nobuo Suganuma, Funabashi, all of Japan

[73] Assignee: Lion Corporation, Tokyo, Japan

[21] Appl. No.: 250,221

[22] Filed: Apr. 2, 1981

[30] Foreign Application Priority Data

Apr. 8, 1981 [JP] Japan ................................. 56-45823

[51] Int. Cl.³ .......................... A61K 7/16; A61K 7/22; A61K 7/26; A61K 9/68
[52] U.S. Cl. ........................................ 424/54; 424/48; 424/49; 424/58
[58] Field of Search .............................. 424/54, 48–58

[56] References Cited

U.S. PATENT DOCUMENTS

| 3,720,762 | 3/1973 | Hatasa | 426/651 |
| 4,272,512 | 6/1981 | Gaffar | 424/47 |
| 4,272,513 | 6/1981 | Gaffar | 424/52 |
| 4,309,410 | 1/1982 | Gaffar | 424/57 |

FOREIGN PATENT DOCUMENTS

| 887315 | 5/1981 | Belgium . |
| 49-39818 | 10/1974 | Japan . |
| 54-129138 | 10/1979 | Japan . |
| 55-19235 | 2/1980 | Japan . |
| 56-142205 | 6/1981 | Japan . |
| 56-110609 | 8/1981 | Japan . |
| 2073019A | 10/1981 | United Kingdom . |

OTHER PUBLICATIONS

Merck Index, 9th Ed., 1976 #1867.
Merck Index, 9th Ed., 1976 #5663.
Jacobs Am. Perf., 61:469–471, Jun. 1953, Flavoring Mouth Washes.
Jacobs Am. Perf., 61:389, 391, 393, May 1953, How to Flavor Toothpaste.

*Primary Examiner*—Shep K. Rose
*Attorney, Agent, or Firm*—Birch, Stewart, Kolasch & Birch

[57] ABSTRACT

An oral composition containing tranexamic acid in which carvone is blended in an amount of 0.1 to 5% by weight and l-menthol may preferably be blended in an amount of 0.03 to 10% by weight. Carvone improves the bitterness inherent to the tranexamic acid-containing oral composition. The composition may preferably contain a mixed humectant of sorbitol and glycerin at a weight ratio of 1:9 to 6:4 and a binder, at least 60% by weight of the binder being an alkali metal salt of carboxymethyl cellulose.

5 Claims, No Drawings

ORAL COMPOSITIONS OF TRANEXAMIC ACID AND CARVONE

BACKGROUND OF THE INVENTION

This invention relates to tranexamic acid-containing oral compositions having a good feeling to use.

Tranexamic acid is a well-known anti-inflammatory and hemostyptic agent. It is proposed in Japanese Patent Publication No. 49-39818 to incorporate tranexamic acid into oral compositions such as dentifrices because tranexamic acid is effective for periodontosis propylaxis.

However, as tranexamic acid inherently tastes bitter, oral compositions containing it are bitter and rough to the palate, giving an undesired feeling when orally applied in practice.

An additional disadvantage of such tranexamic acid-containing oral compositions is that they are unstable and tend to discolor upon aging. It was proposed to add cyclodextrin to tranexamic acid-containing oral compositions to prevent discoloration. In general, known techniques for preventing the discoloration of oral compositions such as dentifrices include the addition of a chelating agent or a polycarboxylic acid derivative. However, these approaches have been unsuccessful. When cyclodextrin is blended in an oral composition, a flavor coexisting in the composition is chemically included by cyclodextrin to reduce the flavoring effect, and as a result, this composition fails to give a refreshing feeling to the mouth when applied thereto. Another problem is a reduction of the net amount of active antiplasmin tranexamic acid due to chemical inclusion of tranexamic acid by cyclodextrin. Further, when a chelating agent or a polycarboxylic acid derivative is blended, a consideration is to be made so as to minimize the absorption of calcium ions by these compounds acting on teeth.

SUMMARY OF THE INVENTION

A primary object of the present invention is to provide a tranexamic acid-containing oral composition which has a soft taste and a favorable feeling on use while its bitterness is minimized.

According to the present invention, there is provided a tranexamic acid-containing oral composition comprising 0.1 to 5% by weight of the composition of carvone.

By blending carvone in a tranexamic acid-containing oral composition in the above-specified amounts, the feeling of the composition on use is improved to an acceptable level. The presence of carvone allows tranexamic acid to be effectively incorporated into oral compositions such as dentifrices as an active ingredient.

In a preferred embodiment of the present invention, l-menthol is used in combination with carvone. Particularly, when carvone and l-menthol are blended at a weight ratio of from 1:9 to 9:1, more preferably from 3:7 to 7:3, not only the composition has an enhanced refreshing action and a further improved feeling to use, but also the aging discoloration of the tranexamic acid-containing oral composition is substantially minimized. The resulting tranexamic acid-containing oral composition is stable, refreshing and favorable.

In another preferred embodiment of the present invention, the tranexamic acid-containing oral composition further comprises a mixed humectant consisting of sorbitol and glycerine at a relative ratio by weight of 1:9 to 6:4 and a binder of which at least 60% by weight is an alkali metal salt of carboxymethyl cellulose. By blending the above mixed humectant and the binder containing at least 60% by weight of an alkali metal salt of carboxymethyl cellulose on the basis of the weight of the binder, the tranexamic acid-containing oral compositions are prevented from discoloring and become more stable. In addition, the action of tranexamic acid or the function of tranexamic acid-containing oral compositions is fully exerted as tranexamic acid and flavors are free from chemically inclusion.

The above and other objects, features and advantages of the present invention will become more apparent and understandable from the following descriptions.

DETAILED DESCRIPTION OF THE INVENTION

The oral composition of the present invention is contemplated to include dentifrices such as toothpastes, toothpowders and liquid dentifrices, liquid oral refreshers such as mouthwashes, solid oral refreshers such as troches, chewing gums, and oral pastes as long as they contain an effective amount of tranexamic acid. According to the first aspect of the present invention, carvone is blended in such an oral composition containing tranexamic acid. Carvone should be blended in an amount of 0.1 to 5%, preferably 0.3 to 3% by weight of the composition. The use of carvone contributes to an improvement in the feeling of the composition by reducing its bitterness due to tranexamic acid and imparting a soft taste to it, although the use of conventional flavors such as l-menthol, eucalyptus oil, strawberry flavor, sage oil, rosemary oil alone or in admixture results in no reduction of the bitterness attributable to tranexamic acid. Less than 0.1% amounts of carvone blended will not fully overcome bitterness and rough taste. Blending more than 5% of carvone is undesired because the pungency of carvone itself becomes sensible. Accordingly, only 0.1 to 5%, preferably 0.3 to 3% of carvone provides tranexamic acid-containing oral compositions with an acceptable soft taste free of bitterness and pungency.

As long as carbone is blended in the above-specified range, any other flavors may also be blended in addition to carvone, including l-menthol, anethole, eugenol, linalool, cineole, limonene, and cinnamic aldehyde alone or in admixture.

Particularly, it is preferred to blend l-menthol in combination with carvone because the combined use of these flavors can not only provide the tranexamic acid-containing compositions with an optimum degree of refrigeration and even improve its feeling on use, particularly in the case of dentifrices, but also improve the stability of the compositions and prevent them from discoloring upon long-term aging. It is preferred from points of view of feeling on use and stability that carvone and l-menthol are present at a relative weight ratio of from 1:9 to 9:1. The best feeling on use including minimum bitterness, soft taste and refreshment as well as the best aging stability result at a relative ratio of carvone to l-menthol of 3:7 to 7:3. It should be noted that the oral composition according to the present invention contains 0.03 to 10% by weight of the composition of l-menthol. Less than 0.03% amounts of l-menthol blended is too small to form a refreshing stable composition. On the other hand, compositions will become too irritative to give a good feeling to use when the amount of l-menthol blended exceeds 10%.

Carvone and l-menthol may be blended into an oral composition in an isolated or synthetic form while essential oils containing carvone or l-menthol may be used, for example, spearmint oil (containing carvone) and peppermint oil (containing l-menthol).

The amount of tranexamic acid blended is not particularly limited in the present invention, but is generally in the range of 0.01 to 5% by weight of the composition. In addition to tranexamic acid, the oral composition of this invention may further include other additional active ingredients, for example, enzymes such as amylase, protease, mutanase, lysozyme, lytic enzyme, etc., fluorine compounds such as alkali metal monofluorophosphates (e.g., disodium monofluorophosphate, dipotassium monofluorophosphate, etc.) and metal fluorides (e.g., sodium fluoride, stannous fluoride, etc.), stannous compounds, chlorhexidine salts, $\epsilon$-aminocaproic acid, aluminum chlorohydroxyallantoinate, dihydrocholesterol, glycyrrhetinates, glycerophosphate, sodium chloride, water-soluble inorganic phosphates (e.g., potassium and sodium salts of orthophosphoric acid, pyrophosphoric acid and polyphosphoric acid) and the like alone or in admixture.

The oral composition of this invention may further include other well-known ingredients depending on a particular type of the composition. Differently stated, the oral composition of this invention may be formulated into any desired form of dentifrices, liquid and solid oral refreshers and oral pastes by a conventional preparation method using suitably selected ingredients.

When the oral composition of the present invention forms a dentifrice composition, it may contain generally 10 to 90% by weight of an abrasive, particularly 20 to 60% by weight of an abrasive in the case of toothpastes. The abrasive may be selected from dicalcium phosphate dihydrate and anhydride, calcium carbonate, calcium pyrophosphate, calcium sulfate, silica, hydrous silicic acid, alumina, aluminum silicate, aluminum hydroxide, insoluble sodium metaphosphate, magnesium tertiary phosphate, magnesium carbonate and synthetic resins, and mixtures thereof.

A humectant may also be blended generally in an amount of 5–85% by weight, including sorbitol, glycerine, ethylene glycol, propylene glycol, 1,3-butylene glycol, polyethylene glycol, xylitol, maltitol, lactitol, etc. and mixtures thereof.

In preparing dentifrice compositions, a binder may be blended generally in an amount of 0.3–5% by weight, including cellulose derivatives such as sodium carboxymethyl cellulose and hydroxyethyl cellulose, carrageenan, alkali metal alginates such as sodium alginate, gums such as veegum and xanthan gum, synthetic binding agents such as polyvinyl alcohol, inorganic binding agents such as silica gel, aluminum silicate gel, etc. and mixtures thereof.

It is preferred in the present invention that the oral composition contains a mixed humectant consisting of sorbitol and glycerine at a relatively weight ratio of from 1:9 to 6:4, and a binder, at least 60% by weight of the binder being an alkali metal salt of carboxymethyl cellulose such as sodium carboxymethyl cellulose. The aging stability of tranexamic acid-containing orgal compositions can be remarkably improved by blending both the humectant and binder so as to meet the above requirements. If the ratio of sorbitol to glycerine is out of the above-defined range, then tranexamic acid-containing oral compositions are likely to discolor upon aging. Similar discoloration occurs and stability decreases if the amount of the alkali metal salt of carboxymethyl cellulose is less than 60% by weight of the total weight of the binder. In this preferred embodiment, the oral composition may advantageously contain 5 to 85% by weight of the composition of the mixed humectant consisting of sorbitol and glycerine, more particularly, 10 to 70% of the mixed humectant in the case of ordinary toothpastes, 50 to 85% in the case of transparent toothpastes, and 5 to 15% in the case of toothpowders.

It is to be noted that propylene glycol may preferably be added as a binder dispersing agent. In such a case, propylene glycol may be blended in an amount of 5% or less, especially 1 to 5% by weight of the composition. Larger amounts of propylene glycol cause tranexamic acid-containing oral compositions to discolor upon aging and impart to them an undesired scorching taste. On the other hand, the binder cannot be effectively dispersed using less than 1% by weight of propylene glycol.

In oral compositions, also included are anionic surfactants such as water-soluble salts of higher alkyl sulfates having 8 to 18 carbon atoms in the alkyl group (e.g., sodium lauryl sulfate and sodium mirystyl sulfate), water-soluble salts of sulfonated monoglycerides of higher fatty acids having 10 to 18 carbon atoms in the fatty acid group (e.g., sodium lauryl monoglyceride sulfonate and sodium coconut monoglyceride sulfonate), $\alpha$-olefine sulfonates, salts of amides of higher fatty acid having 12 to 16 carbon atoms in the fatty acid group with lower aliphatic amino acids (e.g., sodium-N-methyl-N-palmitoyl touride, sodium N-lauroyl sarcosinate, sodium N-acyl amino acid and sodium N-lauroyl-$\beta$-alanine), soaps, etc.; nonionic surfactants such as alkyrol diethanol amides (e.g. lauroyl diethanol amide), stearyl monoglyceride, sucrose fatty acid esters having 12 to 18 carbon atoms in the fatty acid group (e.g. sucrose monolaurate and dilaurate), lactose fatty acid esters, lactitol fatty acid esters, maltitol fatty acid esters, condensates of sorbitan monostearate with approximately 60 moles of ethylene oxide, condensates of ethylene oxide with propylene oxide condensates of propylene glycol and their derivatives (e.g. polyoxyethylene polyoxypropylene monolauryl ester), etc.; amphoteric surfactants such as those of betaine and amine acid types, etc., alone or in admixture in an amount of 0.5–7% by weight; a sweetener such as sodium saccharin, stevioside, neohesperidin dihydrocalcone, thaumatin, glycyrrhizin, perillartine, p-methoxycinnamic aldehyde, etc.; a preservative such as p-hydroxy methyl benzoic acid, p-hydroxy-butyl benzoic acid, etc.; gelatin, peptone and other ingredients. It is to be noted that the parasubstituted benzoic acid preservative should be blended in amounts of 0.3% by weight or less because compositions become too irritative when the amount exceeds 0.3%.

For example, toothpastes may be prepared by kneading the desired ingredients selected from the foregoing ingredients with a proper amount of water or other solvents.

The toothpastes may generally have a pH of 4.5 to 10, preferably 6 to 8.5.

Other types of oral compositions may be prepared in accordance with conventional formulations and methods using a well-known base material.

The thus prepared composition may be ready for use only after it is packed in a suitable container, for example, aluminum tubes, laminate tubes having an aluminum foil laminated with a plastic lamina on either side, plastic tubes, bottles, aerosol containers or the like.

The following examples are illustrative of this invention and are not to be construed to limit the scope of the invention. All percents are by weight.

EXAMPLE 1

Solid mouth refresher compositions having the formulation shown below were prepared while blending the flavors shown in Table 1. Using a panel of specialized members, a sensory test was carried out to determine the feeling of these compositions on actual use. The results are shown in the right column of Table 1.

| Formulation | % |
| --- | --- |
| Lactose | 11.5 |
| Starch | 30 |
| Orris powder | 5 |
| Tranexamic acid | 0.5 |
| Flavor shown in Table 1 | (see Table 1) |
| Gum arabic solution | Balance |
| | 100.0 |

TABLE 1

| Sample No. | Flavor | Amount (%) | Bitterness |
| --- | --- | --- | --- |
| 1 | Carvone | 0.05 | X |
| 2 | " | 0.1 | O |
| 3 | " | 1 | O |
| 4 | " | 3 | O |
| 5 | " | 5 | O |
| 6 | " | 7 | V |
| 7 | l-menthol | 3 | X |
| 8 | Eucalyptus oil | 3 | X |
| 9 | Strawberry flavor | 3 | X |
| 10 | Sage oil | 3 | X |
| 11 | Rosemary oil | 3 | X |
| 12 | — | — | X |

Note 1:
The criteria for evaluating bitterness are as follows.
O: no bitter
Δ: slightly bitter
X: bitter
V: no bitter, but pungent Note 2:
Those refreshers of the same formulation as sample Nos. 7-12, but not containing tranexamic acid did not taste bitter.

As seen from the results of Table 1, carvone is effective for improving the feeling of tranexamic acid-containing oral compositions which otherwise taste bitter and are rough to the palate. The test proves that the shortcomings of tranexamic acid-containing oral compositions, that is, their own bitterness and lack of soft taste are eliminated by blending 0.1 to 5% by weight of carvone therein.

EXAMPLE 2

Using carvone in combination with l-menthol in the respective amounts shown in Table 2, toothpastes having the formulation shown below were prepared. A sensory test was carried out to determine the feeling (bitterness, softness of taste, and refreshment) of these toothpaste on actual use. In addition, a portion of each toothpaste was aged for one month at 60° C. before it was determined for discoloration to evaluate its stability. The results are shown in Table 2.

| Formulation | % |
| --- | --- |
| Propylene glycol | 3 |
| Sodium carboxymethyl cellulose | 0.6 |
| Carrageenan | 0.4 |
| Sorbitol | 5 |
| Glycerine | 12 |
| Sodium saccharin | 0.1 |
| Hydrated silica | 3 |
| Sodium lauryl sulfate | 1.5 |
| Dicalcium phosphate | 45 |
| Tranexamic acid | 0.5 |
| Flavors (carvone and l-menthol) | (see Table 2) |
| Water | Balance |
| | 100.0 |

TABLE 2

| Amount of carvone blended (%) | Amount of l-menthol blended (%) | Bitterness | Softness of taste | Refreshment | Stability (discoloration) |
| --- | --- | --- | --- | --- | --- |
| 1.0 | 0 | O | O | X | Δ |
| 0.9 | 0.1 | O | O | Δ | O |
| 0.7 | 0.3 | O | O | O | O |
| 0.5 | 0.5 | O | O | O | O |
| 0.3 | 0.7 | O | O | O | O |
| 0.1 | 0.9 | Δ | Δ | O | O |
| 0 | 1.0 | X | X | O | O |

The evaluation criterion for each item is as follows.

Bitterness

O: no bitter
Δ: slightly bitter
X: bitter

Softness of taste

O: soft
Δ: moderate
X: rough

Refreshment

O: refreshing
Δ: moderate refreshing
X: unrefreshing

Stability after 60° C., 1 month aging

O: no discoloration
Δ: some discoloration
X: significant discoloration

The results of Table 2 reveals that the combined use of carvone and l-menthol at a relative weight ratio of 1:9 to 9:1, preferably at a relative weight ratio of 3:7 to 7:3, results in tranexamic acid-containing oral compositions which are free of bitterness or rough taste and highly refreshing, and consequently, has a good feeling on use as well as being highly stable as demonstrated by discoloration-free long-term aging.

An additional test was carried out to find that l-menthol may preferably be added in amounts of 0.03 to 10% to give stable oral compositions having a good feeling on use.

EXAMPLE 3

Using sorbitol and glycerine in the relative weight ratios shown in Table 3, toothpastes having the formulation shown below were prepared. The toothpastes were aged for one month at 60° C. before they were determined for discoloration to evaluate their stability. The results are shown in Table 3.

| Formulation | % |
| --- | --- |
| Propylene glycol | 2.5 |
| Humectant (sorbitol and glycerine) | 16.0 |
| Sodium carboxymethyl cellulose | 0.8 |
| Carrageenan | 0.2 |
| Dicalcium phosphate | 45.0 |
| Hydrated silica | 3.0 |
| Sodium lauryl sulfate | 1.5 |
| Sodium saccharin | 0.1 |
| Carvone | 0.3 |
| l-menthol | 0.7 |
| Tranexamic acid | (see Table 3) |
| Water | Balance |
| | 100.0 |

TABLE 3

| Amount of tranexamic acid blended (%) | Stability – Ratio of sorbitol to glycerine (ratio by weight) | | | | | | |
| --- | --- | --- | --- | --- | --- | --- | --- |
| | 100/0 | 85/15 | 70/30 | 50/50 | 30/70 | 15/85 | 0/100 |
| 0 | O | O | O | O | O | O | O |
| 0.5 | X | X | X | O | O | O | X |

The evaluation criterion for stability (discoloration stability) is as follows.
O: no discoloration
Δ: some discoloration
X: significant discoloration The results of Table 3 reveals that aging discoloration is prevented and hence, stability is improved when mixed humectants of sorbitol and glycerine at a relative weight ratio of 1:9 to 6:4 are blended in tranexamic acid-containing oral compositions.

EXAMPLE 4

Toothpastes were prepared using the formulation of Example 3 except that the relative weight ratio of sorbitol to glycerine was fixed to 3:7 and the combined amount of sodium carboxymethyl cellulose (CMC) and carrageenan was 1.0%. The relative weight ratio of CMC to carrageenan was varied as shown in Table 4. The aging stability of the toothpastes was determined as described in Example 3. The results are shown in Table 4.

TABLE 4

| Amount of tranexamic acid blended (%) | Stability – Ratio of CMC to carrageenan (ratio by weight) | | | | | | |
| --- | --- | --- | --- | --- | --- | --- | --- |
| | 10/0 | 8/2 | 6/4 | 5/5 | 4/6 | 2/8 | 0/10 |
| 0 | O | O | O | O | O | O | O |
| 0.5 | O | O | O | X | X | X | X |

The results of Table 4 reveals that the aging stability of tranexamic acid-containing oral compositions is improved when CMC and carrageenan are blended at a ratio of 6:4 to 10:0. It was found that similar results were obtained when carrageenan was replaced by sodium alginate. Accordingly, the aging stability of tranexamic acid-containing oral compositions is improved when sodium carboxymethyl cellulose (CMC) occupies 60% or more of the binder blended.

EXAMPLE 5

Toothpastes were prepared using the formulation of Example 3 except that the relative weight ratio of sorbitol to glycerine was fixed to 3:7 and the amount of propylene glycol blended was varied as shown in Table 5. The aging stability of the toothpastes was determined as described in Example 3. The results are shown in Table 5.

TABLE 5

| Amount of tranexamic acid blended (%) | Stability – Amount of propylene glycol blended (%) | | |
| --- | --- | --- | --- |
| | 3 | 5 | 6 |
| 0 | O | O | O |
| 0.5 | O | O | X |

As seen from Table 5, it is preferred to blend 5% or less of propylene glycol in tranexamic acid-containing oral compositions for improving the stability thereof.

EXAMPLE 6

Toothpaste

| Aluminum hydroxide | 50% |
| --- | --- |
| Hydrated silica | 3% |
| Propylene glycol | 2% |
| Sorbitol | 3% |
| Glycerine | 15% |
| Sodium saccharin | 0.1% |
| Sodium lauryl sulfate | 1.5% |
| Sodium carboxymethyl cellulose | 1.0% |
| Tranexamic acid | 0.1% |
| Carvone | 0.3% |
| l-menthol | 0.7% |
| Water | Balance |
| | 100.0% |

EXAMPLE 7

Toothpaste

| Dicalcium phosphate | 50% |
| --- | --- |
| Propylene glycol | 3% |
| Sorbitol | 5% |
| Glycerine | 12% |
| Sodium saccharin | 0.1% |
| Sodium lauryl sulfate | 1.0% |
| Sucrose monolaurate | 1.0% |
| Carrageenan | 0.3% |
| Sodium carboxymethyl cellulose | 0.7% |
| Sodium monofluorophosphate | 0.76% |
| Tranexamic acid | 0.05% |
| Carvone | 0.5% |
| l-menthol | 0.5% |
| Anethole | 0.1% |
| Water | Balance |
| | 100.0% |

EXAMPLE 8

Powder dentifrice

| Calcium carbonate | 70% |
| --- | --- |
| Sorbitol | 3% |
| Glycerine | 7% |
| Sodium saccharin | 0.1% |
| Sodium lauryl sulfate | 1.5% |
| Tranexamic acid | 0.03% |
| Carvone | 0.8% |
| l-menthol | 0.2% |
| Water | Balance |
| | 100.0% |

EXAMPLE 9

Toothpaste

| | |
|---|---|
| Silica | 20% |
| Propylene glycol | 2% |
| Sorbitol | 20% |
| Glycerine | 40% |
| Sodium saccharin | 0.1% |
| Sodium lauryl sulfate | 1.0% |
| Sucrose monolaurate | 1.0% |
| Lactitol monolaurate | 1.0% |
| Carrageenan | 0.5% |
| Sodium carboxymethyl cellulose | 0.5% |
| Chlorhexidine hydrochloride | 0.01% |
| Tranexamic acid | 0.5% |
| Carvone | 0.6% |
| l-menthol | 0.4% |
| Eugenol | 0.1% |
| Water | Balance |
| | 100.0% |

EXAMPLE 10

Toothpaste

| | |
|---|---|
| Calcium pyrophosphate | 50% |
| Propylene glycol | 4% |
| Sorbitol | 9% |
| Glycerine | 11% |
| Stevioside | 0.1% |
| Dipotassium glycyrrhizinate | 0.05% |
| Lactitol monolaurate | 2.0% |
| Carrageenan | 0.2% |
| Sodium carboxymethyl cellulose | 0.8% |
| Sodium alginate | 0.2% |
| Tranexamic acid | 1.0% |
| Carvone | 0.5% |
| l-menthol | 0.5% |
| Anethole | 0.1% |
| Eugenol | 0.05% |
| Linalool | 0.05% |
| Cineole | 0.05% |
| Water | Balance |
| | 100.0% |

EXAMPLE 11

Liquid dentifrice

| | |
|---|---|
| Glycerine | 35% |
| Propylene glycol | 5% |
| Sodium polyacrylate | 3% |
| Sodium lauryl sulfate | 1% |
| Sodium saccharin | 0.2% |
| Ethanol | 3% |
| Carvone | 1.5% |
| l-menthol | 0.5% |
| Tranexamic acid | 3.0% |
| Water | Balance |
| | 100.0% |

EXAMPLE 12

Mouthwash

| | |
|---|---|
| Ethanol (90%) | 20% |
| Sodium saccharin | 0.3% |
| Polyoxyethylene-hardened castor oil | 0.5% |
| Carvone | 1.5% |
| l-menthol | 1.5% |
| Anethole | 0.2% |
| Eugenol | 0.1% |
| Linalool | 0.1% |
| Cineole | 0.1% |
| Tranexamic acid | 0.05% |
| Water | Balance |
| | 100.0% |

EXAMPLE 13

Troche

| | |
|---|---|
| Gum arabic | 6% |
| Glucose | 72% |
| Carvone | 0.4% |
| l-menthol | 0.1% |
| Spearmint oil | 0.1% |
| Tranexamic acid | 0.1% |
| Water | Balance |
| | 100.0% |

EXAMPLE 14

Chewing gum

| | |
|---|---|
| Gum base | 20% |
| Calcium carbonate | 2% |
| Syrup | 15% |
| Powdered sugar | 60% |
| Carvone | 0.9% |
| l-menthol | 1.5% |
| Anethole | 0.1% |
| Tranexamic acid | 0.5% |
| | 100.0% |

EXAMPLE 15

Oral paste

| | |
|---|---|
| Liquid paraffin | 26% |
| Sorbitol | 5% |
| Glycerine | 15% |
| Cetanol | 4% |
| Paraffin wax | 6% |
| Microcrystalline wax | 10% |
| Polyoxyethylene sorbitan monooleate | 5% |
| Carvone | 0.5% |
| l-menthol | 0.5% |
| Tranexamic acid | 0.1% |
| Water | Balance |
| | 100.0% |

EXAMPLE 16

Solid mouth refresher

| | |
|---|---|
| Lactose | 11% |
| Starch | 40% |
| Orris powder | 5% |
| Gum arabic solution | 40% |
| Carvone | 3% |
| Tranexamic acid | 1% |
| | 100.0% |

The oral compositions of Examples 6 to 16 were found to give a good feeling on use and be stable even after long-term aging.

What is claimed is:

1. An oral composition for topical use having an effective anti-inflammatory and hemostyptic amount of tranexamic acid, consisting essentially of:
   0.01 to 5% by weight of tranexamic acid;
   0.1 to 5% by weight of carvone;
   0.03 to 10% by weight of l-menthol wherein the weight ratio of carvone and l-menthol is in the range of from 3:7 to 7:3;
   5 to 85% by weight of a mixed humectant of sorbitol and glycerine blended at a weight ratio of 1:9 to 6:4;
   0.3 to 5% by weight of a binder containing at least 60% by weight of an alkali metal salt of carboxymethyl cellulose; and
   not less than 1% and not more than 5% by weight of propylene glycol wherein the oral composition exhibits reduced bitterness due to the tranexamic acid and exhibits good storage stability upon long-term aging said composition avoiding the discoloration upon aging, and undesired scorching taste, imparted by more than 5% by weight of propylene glycol to tranexamic acid containing oral compositions.

2. An oral composition according to claim 1, wherein the carvone and l-menthol are blended at a weight ratio of 3:7 to 7:3.

3. An oral composition according to claim 1, which further contains a mixed humectant of sorbitol and glycerine blended at a weight ratio of 1:9 to 6:4 and a binder, at least 60% by weight of the binder being an alkali metal salt of carboxymethyl cellulose.

4. An oral composition according to claim 1, wherein a mixed humectant of sorbitol and glycerine blended at a weight ratio of 1:9 to 6:4 is present in an amount of 5 to 85% by weight of the composition and wherein the composition contains 0.3 to 5% by weight of the composition of a binder containing at least 60% by weight of an alkali metal salt of carboxymethyl cellulose.

5. An oral composition for topical use comprising: 0.01 to 5% by weight of tranexamic acid; 0.1 to 5% by weight of carvone; 0.03 to 10% by weight of l-menthol; not less than 1% and not more than 5% by weight of propylene glycol; and a carrier, wherein the weight ratio of carvone and l-menthol is in the range of from 1:9 to 9:1 wherein the oral composition exhibits reduced bitterness due to the tranexamic acid and exhibits good storage stability upon long-term aging said composition avoiding the discoloration upon aging, and undesired scorching taste, imparted by more than 5% by weight of propylene glycol to tranexamic acid containing oral compositions.

* * * * *

UNITED STATES PATENT AND TRADEMARK OFFICE
CERTIFICATE OF CORRECTION

PATENT NO. : 4,465,662
DATED : August 14, 1984
INVENTOR(S) : Nobuo Suganuma

It is certified that error appears in the above-identified patent and that said Letters Patent is hereby corrected as shown below:

On the cover page of the patent, left hand column, item No. 75, delete:

Hiroshi Sato, Tokyo;
Haruo Watanabe, Higashikurume;

Signed and Sealed this

Twenty-first Day of May 1985

[SEAL]

Attest:

DONALD J. QUIGG

*Attesting Officer*   *Acting Commissioner of Patents and Trademarks*